US007587238B2

United States Patent
Moffitt et al.

(10) Patent No.: US 7,587,238 B2
(45) Date of Patent: *Sep. 8, 2009

(54) COMBINED NEURAL STIMULATION AND CARDIAC RESYNCHRONIZATION THERAPY

(75) Inventors: Julia Moffitt, North Liberty, IA (US); Sophia Wang, New Brighton, MN (US); Bruce H. KenKnight, Maple Grove, MN (US); Imad Libbus, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 614 days.

This patent is subject to a terminal disclaimer.

(21) Appl. No.: 11/078,460

(22) Filed: Mar. 11, 2005

(65) Prior Publication Data

US 2006/0206154 A1    Sep. 14, 2006

(51) Int. Cl.
*A61N 1/00*    (2006.01)
(52) U.S. Cl. .......................................................... 607/9
(58) Field of Classification Search ................. 607/2, 607/3, 4, 9, 17–19, 23, 28
See application file for complete search history.

(56) References Cited

U.S. PATENT DOCUMENTS

| 4,142,530 A | 3/1979 | Wittkampf |
| 4,936,304 A | 6/1990 | Kresh et al. |
| 5,024,222 A | 6/1991 | Thacker |
| 5,111,815 A | 5/1992 | Mower |
| 5,190,035 A | 3/1993 | Salo et al. |
| 5,199,428 A | 4/1993 | Obel et al. |
| 5,203,326 A | 4/1993 | Collins |
| 5,275,826 A | 1/1994 | Badylak et al. |
| 5,507,784 A | 4/1996 | Hill et al. |

(Continued)

FOREIGN PATENT DOCUMENTS

EP    1304135 A2    4/2003

(Continued)

OTHER PUBLICATIONS

Abraham, W T., "Miracle Study Group, Multicenter InSync Randomized Clinical Evaluation, Cardiac resynchronization in chronic heart failure", *New England Journal of Medicine*, 346(24), (Jul. 13, 2002), 1845-53.

(Continued)

*Primary Examiner*—George Manuel
(74) *Attorney, Agent, or Firm*—Schwegman, Lundberg & Woessner, P.A.

(57) ABSTRACT

Methods and devices for delivering cardiac therapy to a patient are provided. Various implantable device embodiments comprise a plurality of leads and a controller. The leads include at least one lead to be positioned within a lead path to deliver ventricular pacing pulses and to deliver neural stimulation at a site proximate to the heart to inhibit sympathetic nerve activity. The controller controls delivery of the ventricular pacing pulses in accordance with a programmed pacing mode and controls delivery of the neural stimulation. The controller is programmed to deliver remodeling control therapy (RCT) by delivering ventricular pacing to pre-excite a ventricular myocardium region to mechanically unload that region during systole, and further is programmed to deliver anti-remodeling therapy (ART) by delivering neural stimulation to inhibit sympathetic nerve activity in conjunction with RCT. Other embodiments are provided herein.

42 Claims, 6 Drawing Sheets

U.S. PATENT DOCUMENTS

| | | |
|---|---|---|
| 5,514,174 A | 5/1996 | Heil, Jr. et al. |
| 5,522,854 A | 6/1996 | Ideker et al. |
| 5,700,282 A | 12/1997 | Zabara |
| 5,755,766 A | 5/1998 | Chastain et al. |
| 5,873,898 A | 2/1999 | Hemming et al. |
| 5,902,324 A | 5/1999 | Thompson et al. |
| 6,006,122 A | 12/1999 | Smits |
| 6,073,048 A | 6/2000 | Kieval et al. |
| 6,119,043 A | 9/2000 | Hsu et al. |
| 6,134,470 A | 10/2000 | Hartlaub |
| 6,161,042 A | 12/2000 | Hartley et al. |
| 6,292,695 B1 | 9/2001 | Webster, Jr. et al. |
| 6,351,668 B1 | 2/2002 | Chen |
| 6,353,757 B2 | 3/2002 | Chen |
| 6,366,814 B1 | 4/2002 | Boveja et al. |
| 6,377,856 B1 | 4/2002 | Carson |
| 6,398,800 B2 | 6/2002 | Chen |
| 6,408,213 B1 | 6/2002 | Bartig et al. |
| 6,544,270 B1 | 4/2003 | Zhang |
| 6,549,813 B2 | 4/2003 | Audoglio |
| 6,564,096 B2 | 5/2003 | Mest |
| 6,567,704 B2 | 5/2003 | Sundquist et al. |
| 6,574,512 B1 | 6/2003 | Zhang et al. |
| 6,584,362 B1 | 6/2003 | Scheiner et al. |
| 6,634,364 B2 | 10/2003 | Westlund et al. |
| 6,647,291 B1 | 11/2003 | Bonner et al. |
| 6,839,592 B2 * | 1/2005 | Grandjean ............ 607/9 |
| 6,882,886 B1 | 4/2005 | Witte et al. |
| 6,922,585 B2 | 7/2005 | Zhou et al. |
| 6,937,896 B1 | 8/2005 | Kroll |
| 6,942,622 B1 | 9/2005 | Turcott |
| 6,988,007 B1 | 1/2006 | Morgan et al. |
| 7,025,730 B2 | 4/2006 | Cho et al. |
| 7,069,070 B2 | 6/2006 | Carlson et al. |
| 7,092,755 B2 | 8/2006 | Florio |
| 7,123,961 B1 | 10/2006 | Kroll et al. |
| 7,139,607 B1 | 11/2006 | Shelchuk |
| 7,191,015 B2 | 3/2007 | Lamson et al. |
| 7,260,431 B2 * | 8/2007 | Libbus et al. ............ 607/4 |
| 7,277,761 B2 | 10/2007 | Shelchuk |
| 7,333,854 B1 | 2/2008 | Brewer et al. |
| 2002/0016550 A1 | 2/2002 | Sweeney et al. |
| 2002/0026228 A1 | 2/2002 | Schauerte |
| 2002/0035378 A1 | 3/2002 | Bardy et al. |
| 2002/0058877 A1 | 5/2002 | Baumann et al. |
| 2002/0091415 A1 | 7/2002 | Lovett et al. |
| 2002/0116030 A1 | 8/2002 | Rezai |
| 2002/0120304 A1 | 8/2002 | Mest |
| 2002/0188326 A1 | 12/2002 | Zheng et al. |
| 2003/0004549 A1 | 1/2003 | Hill et al. |
| 2003/0040774 A1 | 2/2003 | Terry et al. |
| 2003/0060857 A1 | 3/2003 | Perrson et al. |
| 2003/0060858 A1 | 3/2003 | Kieval et al. |
| 2003/0078623 A1 | 4/2003 | Weinberg et al. |
| 2003/0078629 A1 | 4/2003 | Chen |
| 2003/0100924 A1 | 5/2003 | Foreman et al. |
| 2003/0181958 A1 | 9/2003 | Dobak, III |
| 2003/0181959 A1 | 9/2003 | Dobak, III |
| 2003/0199958 A1 | 10/2003 | Zhang et al. |
| 2003/0236575 A1 | 12/2003 | Yu et al. |
| 2004/0015193 A1 | 1/2004 | Lamson et al. |
| 2004/0049235 A1 | 3/2004 | Deno et al. |
| 2004/0054381 A1 | 3/2004 | Pastore et al. |
| 2004/0088015 A1 | 5/2004 | Casavant et al. |
| 2004/0098057 A1 | 5/2004 | Pastore |
| 2004/0116970 A1 | 6/2004 | Girouard et al. |
| 2004/0122496 A1 | 6/2004 | Zhang et al. |
| 2004/0122497 A1 | 6/2004 | Zhang et al. |
| 2004/0122498 A1 | 6/2004 | Zhang et al. |
| 2004/0172075 A1 | 9/2004 | Shafer et al. |
| 2004/0199210 A1 | 10/2004 | Shelchuk |
| 2004/0260374 A1 | 12/2004 | Zhang et al. |
| 2004/0260375 A1 | 12/2004 | Zhang et al. |
| 2005/0059897 A1 | 3/2005 | Snell et al. |
| 2005/0065554 A1 | 3/2005 | KenKnight et al. |
| 2005/0065555 A1 | 3/2005 | Er |
| 2005/0096705 A1 | 5/2005 | Pastore et al. |
| 2005/0143785 A1 | 6/2005 | Libbus |
| 2005/0149126 A1 | 7/2005 | Libbus |
| 2005/0149127 A1 | 7/2005 | Libbus |
| 2005/0149128 A1 * | 7/2005 | Heil et al. ............ 607/9 |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149155 A1 | 7/2005 | Schneier et al. |
| 2005/0149156 A1 | 7/2005 | Libbus et al. |
| 2005/0154418 A1 | 7/2005 | Kieval et al. |
| 2005/0222632 A1 * | 10/2005 | Obino ............ 607/28 |
| 2005/0261741 A1 | 11/2005 | Libbus et al. |
| 2006/0095080 A1 | 5/2006 | Libbus et al. |
| 2006/0106429 A1 | 5/2006 | Libbus et al. |
| 2006/0134071 A1 | 6/2006 | Ross et al. |
| 2006/0136027 A1 | 6/2006 | Westlund et al. |
| 2006/0136028 A1 | 6/2006 | Ross et al. |
| 2006/0195038 A1 | 8/2006 | Carlson et al. |
| 2006/0206153 A1 | 9/2006 | Libbus et al. |
| 2006/0206159 A1 | 9/2006 | Moffitt et al. |
| 2006/0224188 A1 | 10/2006 | Libbus et al. |
| 2006/0253156 A1 | 11/2006 | Pastore et al. |
| 2007/0038261 A1 | 2/2007 | Kieval et al. |
| 2007/0067008 A1 | 3/2007 | Schneier et al. |
| 2007/0123923 A1 | 5/2007 | Lindstrom et al. |
| 2008/0015648 A1 | 1/2008 | Libbus et al. |

FOREIGN PATENT DOCUMENTS

| | | |
|---|---|---|
| EP | 1421973 A2 | 5/2004 |
| WO | WO-9965561 A1 | 12/1999 |
| WO | WO-02085448 A2 | 10/2002 |
| WO | WO-02087694 A1 | 11/2002 |
| WO | WO-03011388 A2 | 2/2003 |
| WO | WO-03020364 A2 | 3/2003 |
| WO | WO-03082080 A2 | 10/2003 |
| WO | WO-03082080 A3 | 10/2003 |
| WO | WO-2004012814 A1 | 2/2004 |
| WO | WO-2004033036 A2 | 4/2004 |
| WO | WO-2005065771 A1 | 7/2005 |
| WO | WO-2005113066 A1 | 12/2005 |
| WO | WO-2006098996 A1 | 9/2006 |

OTHER PUBLICATIONS

Andersen, H , "Long-term follow-up of patients from a randomised trial of atrial versus ventricular pacing for sick-sinus syndrome", *Lancet*, 350(9086), (Oct. 25, 1997), 1210-6.

Behrens, S. , "Effects of Amiodarone on the Circadian Pattern of Sudden Cardiac Death (Department of Vererans Affairs Congestive Heart Failure-Survival Trial of Antiarrhythmic Therapy)", *Am. J. Cardiol.*, 80(1), (Jul. 1997), 45-48.

Behrens, S. , "Modification of the Circadian Pattern of Ventricular Tachyarrhythmias by Beta-Blocker Therapy", *Clin. Cardiol.*, 20(3), (Mar. 1997), 253-257.

Benchimol, A , "Cardiac hemodynamics during stimulation of the right atrium, right ventricle, and left ventricle in normal and abnormal hearts", *Circulation*, 33(6), (Jun. 1966), 933-44.

Bilgutay, A M., "A new concept in the treatment of hypertension utilizing an implantable electronic device: "Baropacer"", *Trans Am Soc Artif Intern Organs,*, 10, (1964), 387-395.

Bocker, D. , "Ventricular Resynchronization Therapy May Restore Autonomic Balance as Evidenced by Redicung the Low Frequency to High Frequency Autonomic Ratio in Heart Failure Patients", *4th*

*International Meeting organized by the Working Group on Heart Failure of the European Society of Cardiology*(Abstract), Barcelona, Spain,(Jun. 11, 2001), 1 p.

Chapleau, M W., "Neuro-cardiovascular regulation: from molecules to man, Introduction.", *Annals of the New York Academy of Sciences*, 940, (Jun. 2001),xiii-xxii.

Chapleau, M W., et al., "Pulsatile activation of baroreceptors causes central facilitation of baroreflex", *American Journal of Physiology*, 256(6 Pt 2), (Jun. 1989),H1735-41.

Dickerson, L W., "Parasympathetic neurons in the cranial medial ventricular fat pad on the dog heart selectively decrease ventricular contractility", *Journal of the Autonomic Nervous System*, 70(1-2), (May 28, 1998), 129-41.

Diedrich, A , "Analysis of raw microneurographic recordings based on wavelet de-noising technique and classification algorithm: wavelet analysis in microneurography", *IEEE Transactions on Biomedical Engineering*, 50(1), (Jan. 2003),41-50.

Gatti, P J., "Vagal control of left ventricular contractility is selectively mediated by a cranioventricular intracardiac ganglion in the cat", *Journal of the Autonomic Nervous System*, vol. 66, No. 3, (Oct. 13, 1997),138-144.

Hayano, J. , "Circadian Rhythms of Atrioventricular Conduction Properties in Chronic Atrial Fibrillation With and Without Heart Failure", *JACC*, 31 (1), (Jan. 1998),pp. 158-166.

Heil, Jr., Ronald W., et al., "Barorelflex Stimulation System to Reduce Hypertension", U.S. Appl. No. 10/746,134, filed Dec. 24, 2003, 78 pgs.

Henning, R J., "Effects of autonomic nerve stimulation, asynchrony, and load on dP/dtmax and on dP/dtmin", *American Journal of Physiology*, 260(4 Pt 2), (Apr. 1991),H1290-8.

Henning, R J., "Vagal nerve stimulation increases right ventricular contraction and relaxation and heart rate", *Cardiovascular Research*, 32(5), (Nov. 1996),846-53.

Henning, R J., "Vagal stimulation attenuates sympathetic enhancement of left ventricular function", *American Journal of Physiology*, 258(5 Pt 2), (May 1990),H1470-5.

Holder, L K., "Treatment of refractory partial seizures: preliminary results of a controlled study", *Pacing & Clinical Electrophysiology*, 15(10 Pt 2), (Oct. 1992), 1557-71.

Hood Jr., W B., et al., "Asynchronous contraction due to late systolic bulging at left ventricular pacing sites", *American Journal of Physiology*, 217(1), (Jul. 1969),215-21.

Ishise, H , "Time course of sympathovagal imbalance and lift ventricular dysfunction in conscious dogs with heart failure", *Journal of Applied Physiology*, 84(4), (Apr. 1998), 1234-41.

Karpawich, P P., et al., "Altered cardiac histology following apical right ventricular pacing in patients with congenital atrioventricular block", *Pacing Clin Electrophysiol.*, 22(9), (Sep. 1999),1372-7.

Kendrick, J E., "A comparison of the cardiovascular responses to stimulation of the aortic and carotid sinus nerves of the dog", *Proceedings of the Society for Experimental Biology & Medicine*, 144(2), (Nov. 1973),404-11.

Leclercq, C , et al., "Hemodynamic importance of preserving the normal sequence of ventricular activation in permanent cardiac pacing", *Am Heart J.*, 129(6), (Jun. 1995),1133-41.

Libbus, Imad , "Implantable Device for Treating Epilepsy and Cardiac Rhythm Disorders", U.S. Appl. No. 11/312,178, filed Dec. 21, 2005, 39 Pages.

Libbus, I. , "Integrated Lead for Applying Cardiac Resynchronization Therapy and Neural Stimulation Therapy", U.S. Appl. No. 11/077,970, filed Mar. 11, 2005, 67 pgs.

Libbus, Imad , et al., "System and Method for Filtering Neural Stimulation", U.S. Appl. No. 10/982,001, filed Nov. 4, 2004, 58 pgs.

Moffitt, Julia , "Combined Neural Stimulation and Cardiac Resynchronization Therapy", U.S. Appl. No. 11/078,460, filed Mar. 11, 2005, 35 pgs.

Neistadt, A , "Effects of electrical stimulation of the carotid sinus nerve in reversal of experimentally induced hypertension", *Surgery*, 61(6), (Jun. 1967),923-31.

Nolan, James , et al., "Prospective study of heart rate variability and mortality in chronic heart failure: results of the United Kingdom heart failure evaluation and assessment of risk trial (UK-heart).", *Circulation*, vol. 98, No. 15, (Oct. 13, 1998), 1510-1516.

Pappone, Carlo , et al., "Pulmonary Vein Denervation Enhances Long-Term", *Circulation*. 2004;109:327-334, (Jan. 27, 2004),327-334.

Philbin, D M., "Inappropriate shocks delivered by an ICD as a result of sensed potentials from a transcutaneous electronic nerve stimulation unit", *Pacing & Clinical Electrophysiology*, 21(10), (Oct. 1998),2010-1.

Rosenqvist, M , "The effect of ventricular activation sequence on cardiac performance during pacing", *Pacing and Electrophysiology*, 19(9), (1996), 1279-1286.

Ross, Jeffrey , "Epicardial Patch Including Isolated Extracellular Matrix With Pacing Electrodes", U.S. Appl. No. 11/017,627, filed Dec. 20, 2004, 87 pgs.

Ross, Jeffrey , et al., "Use of Extracellular Matrix and Electrical Therapy", U.S. Appl. No. 11/017,237, filed Dec. 20, 2004, 89 pgs.

Schauerte, P , "Catheter stimulation of cardiac parasympathetic nerves in humans: a novel approach to the cardiac autonomic nervous sytem", *Circulation*, 104(20), (Nov. 13, 2001),2430-5.

Schauerte, Patrick , et al., "Focal Atrial Fibrillation: Experimental Evidence for a", *Journal of Cardiovascular Electrophysiology*, vol. 12, No. 5, (May 2001),592-599.

Scheiner, Avram , et al., "Leads for Pacing and/or Sensing the Heart from Within the Coronary Veins", U.S. Appl. No. 11/600,807, filed Nov. 16, 2006, 43 Pages.

Schmidt, E M., "Blood pressure response to aortic nerve stimulation in swine", *American Journal of Physiology*, 215(6), (Dec. 1968), 1488-92.

Sigurdsson, Axel , "The role of neurohormonal activation in chronic heart failure and postmyocardial infarction", *American Heart Journal*, 132 (1 Pt 2 Su), (Jul. 1996),229-234.

Sih, Harris J., "Implantable Medical Devices Comprising Isolated Extracellular Matrix", U.S. Appl. No. 11/017,432, filed Dec. 20, 2004, 87 pgs.

Thompson, Gregory W., "Bradycardia induced by intravascular versus direct stimulation of the vagus nerve", *Annals of Thoracic Surgery*, 65(3), (Mar. 1998),637-642.

Tse, H F ., et al., "Long-term effect of right ventricular pacing on myocardial perfusion and function", *J Am Coll Cardiol.*, 29(4), (Mar. 15, 1997),744-9.

Vanoli, Emilio , "Vagal stimulation and prevention of sudden death in conscious dogs with a healed myocardial infarction", *Circulation Research*, vol. 68, No. 5, (May 1991),1471-1481.

Westlund, Randy , "Lead Electrode Incorporating Extracellular Matrix", U.S. Appl. No. 11/017,238, filed Dec. 20, 2004, 85 pgs.

Wiggers, C J., et al., "The muscular reactions of the mammalian ventricles to artificial surface stimuli", *American Journal of Physiology*, (1925),346-378.

Zamotrinsky, A V., et al., "Vagal neurostimulation in patients with coronary artery disease", *Autonomic Neuroscience-Basic & Clinical*, 88(1-2), (Apr. 12, 2001),109-116.

"U.S. Appl. No. 10/700,368 Non Final office action mailed May 3, 2007", 11 pgs.

"U.S. Appl. No. 10/700,368 Non Final office action mailed Jul. 12, 2006", 19 pgs.

"U.S. Appl. No. 10/700,368 Response filed Nov. 13, 2006 to Non Final office action mailed Jul. 12, 2006", 7 pgs.

"U.S. Appl. No. 10/700,368, Response filed Jan. 31, 2008 to Final Office Action mailed Oct. 31, 2007", 8 pgs.

"U.S. Appl. No. 10/700,368, Response filed Sep. 4, 2007 to Non-Final Office Action mailed May 3, 2007", 8 pgs.

"U.S. Appl. No. 10/700,368 Non-Final Office Action mailed Mar. 14, 2008", OARN, 13 pgs.

"U.S. Appl. No. 10/700,368 Final Office Action mailed Oct. 31, 2007", 12 pgs.

"U.S. Appl. No. 10/850,341 Non Final Office Action mailed May 31, 2006", 9 pgs.

"U.S. Appl. No. 10/850,341 Notice of Allowance mailed Apr. 5, 2007", 7 pgs.

"U.S. Appl. No. 10/850,341 Notice of Allowance mailed Nov. 30, 2006", 8 pgs.

"U.S. Appl. No. 10/850,341 Response filed Oct. 2, 2006 to Non Final Office Action mailed May 31, 2006", 10 pgs.

"U.S. Appl. No. 11/077,970 Non-Final office Action mailed Feb. 27, 2008", 12 pgs.

"U.S. Appl. No. 10/700,368, Response filed Jan. 15, 2009 to Final Office Action mailed Oct. 15, 2008", 8 pgs.

"U.S. Appl. No. 10/700,368, Response filed Jun. 16, 2008 to Non-Final Office Action mailed Mar. 14, 2008", 8 pgs.

"U.S. Appl. No. 10/700,368 Final Office Action mailed Oct. 15, 2008", 12 pgs.

"U.S. Appl. No. 11/077,970 Response filed May 27, 2008 to Office Action mailed Feb. 27, 2008", 12 pages.

"U.S. Appl. No. 11/077,970 Final Office Action mailed Oct. 21, 2008", 10 pgs.

* cited by examiner

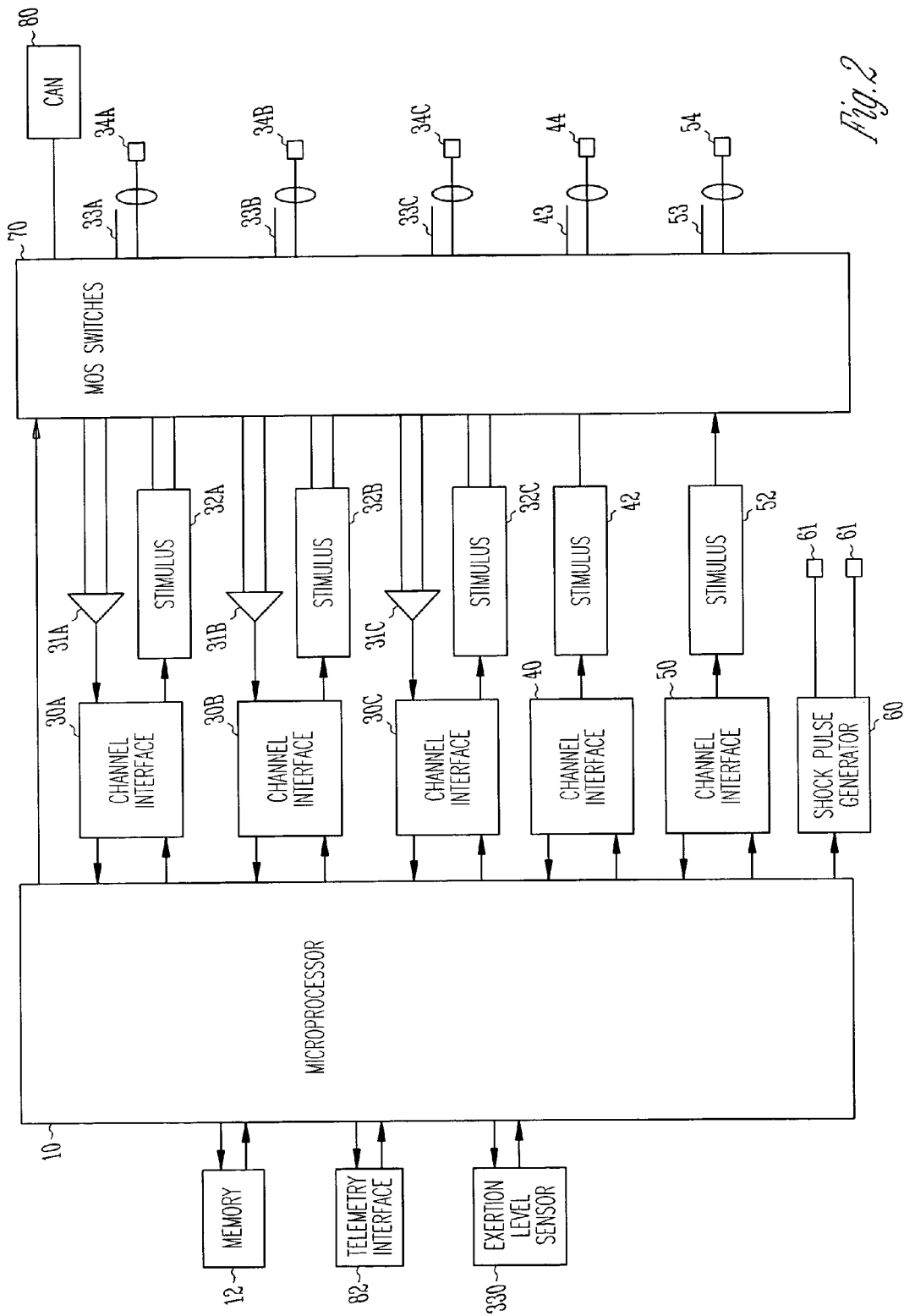

COMBINED NEURAL STIMULATION AND CARDIAC RESYNCHRONIZATION THERAPY

RELATED APPLICATIONS

This patent application is related to the following co-pending and commonly assigned U.S. Patent Applications, the disclosures of which are herein incorporated by reference in their entirety: "Multi-Site Ventricular Pacing Therapy With Parasympathetic Stimulation," Ser. No. 10/700,368, filed Nov. 3, 2003; "Lead for Stimulating the Baroreceptors in the Pulmonary Artery," Ser. No. 10/746,861, filed Dec. 24, 2003; "Combined Remodeling Control Therapy and Anti-Remodeling Therapy By Implantable Cardiac Device," Ser. No. 10/850,341, filed May 20, 2004, now issued as U.S. Pat. No. 7,260,431; and "Integrated Lead for Applying Cardiac Resynchronization Therapy and Neural Stimulation Therapy;" Ser. No. 11/077,970, filed Mar. 11, 2005.

FIELD OF THE INVENTION

This patent application pertains to methods and apparatus for the treatment of cardiac disease. In particular, it relates to methods and apparatus for improving cardiac function with electro-stimulatory therapy.

BACKGROUND

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

BRIEF DESCRIPTION OF THE DRAWINGS

FIG. 2 is a system diagram of a cardiac device configured for multi-site stimulation and sensing.

DETAILED DESCRIPTION

Figure 1A:
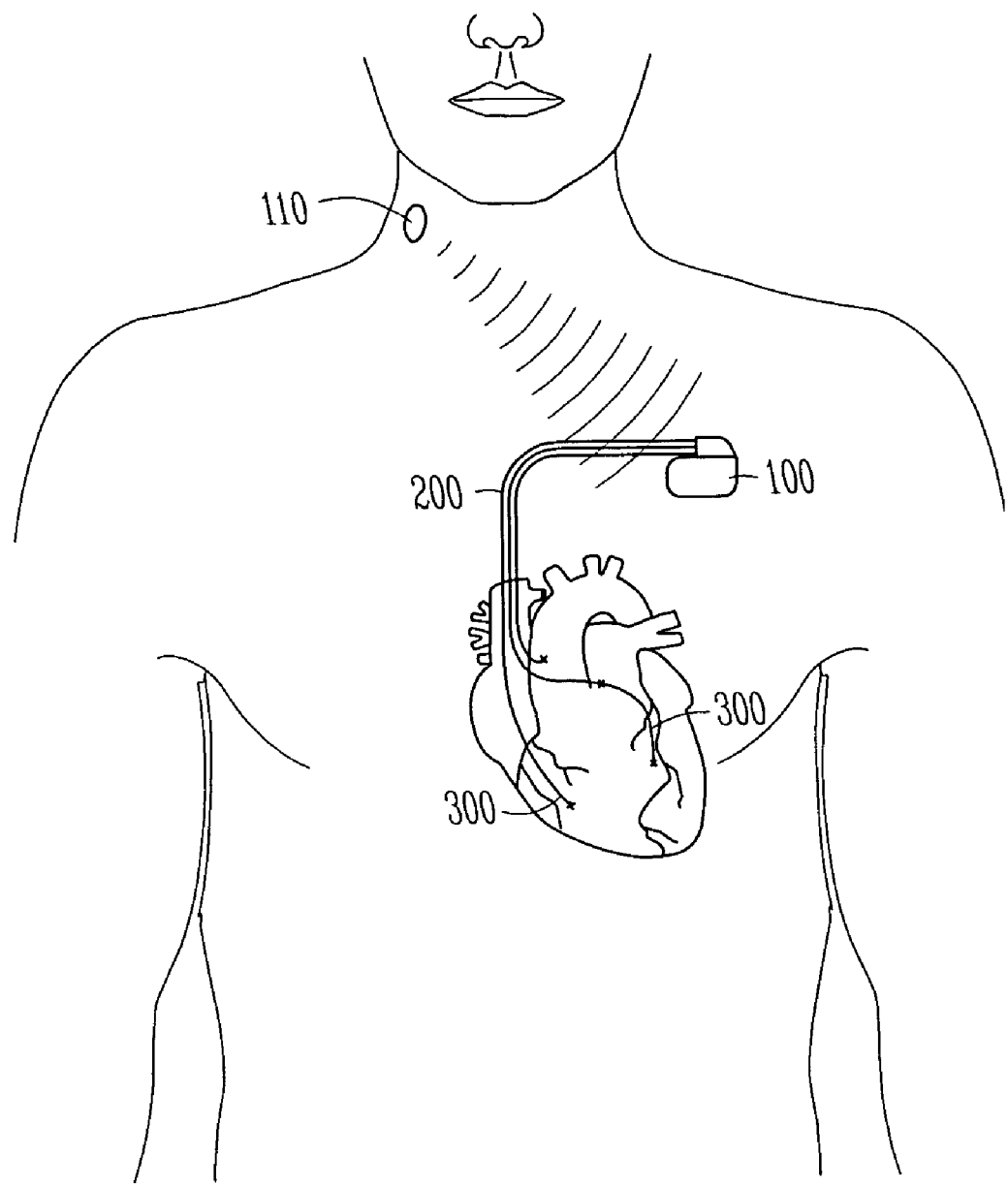
FIGS. 1A-E illustrate embodiments of the present subject matter in relation to a heart.

Clinical data has shown that cardiac resynchronization therapy (CRT), achieved through synchronized biventricular pacing, results in a significant improvement in cardiac function. It has also been reported CRT can be beneficial in preventing and/or reversing the ventricular remodeling that often occurs in post-MI and heart failure patients. As explained in detail below, the present subject matter relates to an implantable cardiac device capable of providing remodeling control therapy (RCT) by controlling ventricular activation with cardiac resynchronization pacing and providing anti-remodeling therapy (ART) by stimulating the baroreflex in order to inhibit sympathetic activity. The combined application of these two therapies provides a greater therapeutic benefit than either of them individually. The device controls ventricular activation through synchronized pacing of the right and left ventricles. In addition, the device may provide a combination of parasympathetic stimulation and sympathetic inhibition. Parasympathetic stimulation can be achieved through a nerve cuff electrode placed around the cervical vagus nerve bundle, while sympathetic inhibition can be achieved through baroreflex stimulation, either through a nerve cuff electrode placed around the aortic or carotid sinus nerve, or though a stimulation lead designed to stimulate barorecptors in the pulmonary artery. The device controls the delivery of RCT and ART independently in either an open-loop or closed-loop fashion, the latter based upon a cardiac function assessment performed by the device.

1. Remodeling Control Therapy by Cardiac Resynchronization Pacing

Implantable cardiac devices that provide electrical stimulation to selected chambers of the heart have been developed in order to treat a number of cardiac disorders. A pacemaker, for example, is a device which paces the heart with timed pacing pulses, most commonly for the treatment of bradycardia where the ventricular rate is too slow. Atrio-ventricular conduction defects (i.e., AV block) and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate. Implantable devices may also be used to treat cardiac rhythms that are too fast, with either anti-tachycardia pacing or the delivery of electrical shocks to terminate atrial or ventricular fibrillation.

Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

It has also been found that CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle in a manner which causes a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur.

2. Anti-Remodeling Therapy by Modulating Autonomic Activity

As noted above, activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. The present subject matter employs electrostimulatory means to modulate autonomic activity, referred to as anti-remodeling therapy or ART. When delivered in conjunction with ventricular resynchronization pacing, such modulation of autonomic activity acts synergistically to reverse or prevent cardiac remodeling.

3. Device Embodiments

Figure 1C:
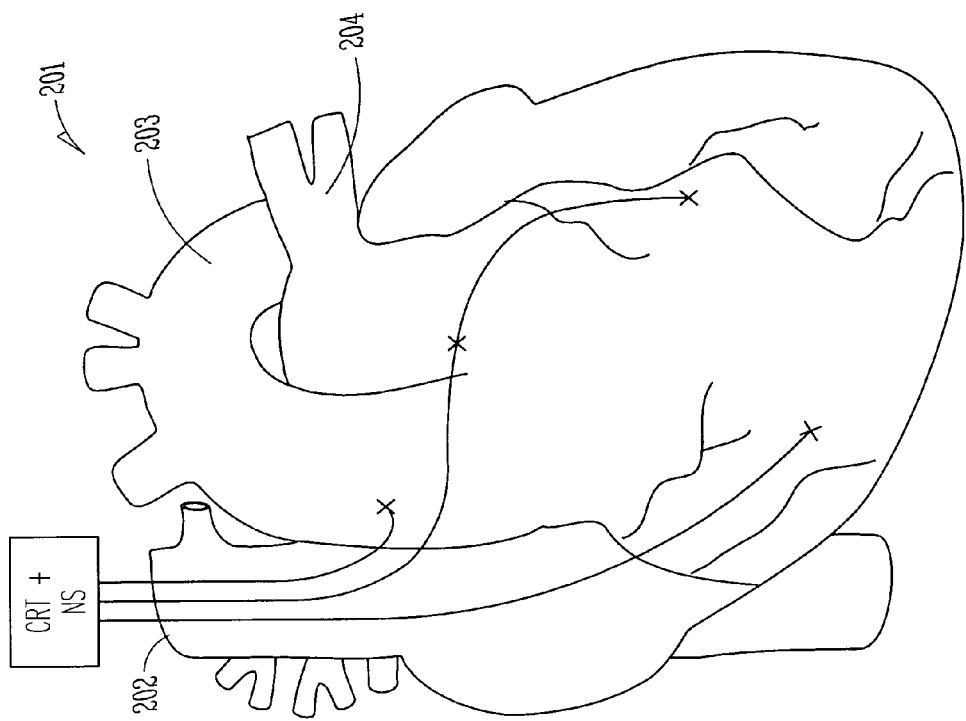
Figure 1B:
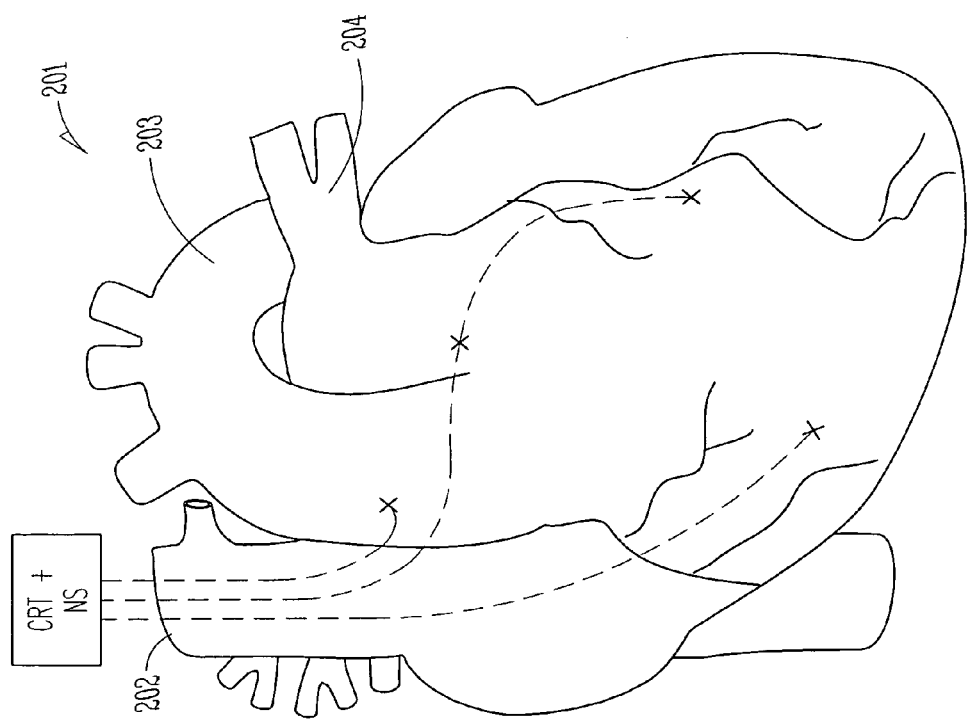

FIGS. 1A-1C illustrate some device embodiments. FIG. 1A illustrates CRT performed by an implantable cardiac device and neural stimulation performed by a satellite unit. FIG. 1B illustrates an implantable medical device to perform both CRT and neural stimulation therapy using leads represented by the dotted lines and electrodes represented by "X" fed into the right atrium, right ventricle, and coronary sinus of the heart. FIG. 1C illustrates an implantable medical device with using leads represented by the dotted lines and electrodes represented by "X" epicardially positioned to perform both CRT and neural stimulation therapy. With respect to FIGS. 1B and 1C, the CRT leads can be separate from the neural stimulation leads in some embodiments, and the CRT leads can be integrated with the neural stimulation leads in other embodiments. In the embodiments illustrated in FIGS. 1B and 1C, a right atrium lead, a right ventricle lead and a left ventricle lead are used to perform CRT functions, and the left ventricle lead further includes a neural stimulator, such as an electrode placed in or near the coronary sinus or epicardially placed near a fat pad.

As shown in FIG. 1A, an implantable cardiac device 100 for delivering CRT is typically placed subcutaneously or submuscularly in a patient's chest with leads 200 threaded intravenously into the heart to connect the device to electrodes 300 used for sensing and pacing of the atria and/or ventricles. Electrodes may also be positioned on the epicardium by various means. A programmable electronic controller causes the pacing pulses to be output in response to lapsed time intervals and sensed electrical activity (i.e., intrinsic heart beats not as a result of a pacing pulse). The device senses intrinsic cardiac electrical activity through a sensing channel which incorporates internal electrodes disposed near the chamber to be sensed. A depolarization wave associated with an intrinsic contraction of the atria or ventricles that is detected by the device is referred to as an atrial sense or ventricular sense, respectively. In order to cause such a contraction in the absence of an intrinsic beat, a pacing pulse with energy above a certain threshold is delivered to the chamber through a pacing channel which incorporates internal electrodes disposed near the chamber to be paced. Also shown in the FIG. 1A is a satellite unit 110 which incorporates electrodes for neural stimulation and which communicates with the device 100 via a wireless link. As disclosed herein, the satellite unit 110 is capable of being positioned in a number of locations, including intravascularly and epicardially, to provide desired neural stimulation.

FIG. 2 shows a system diagram of an exemplary microprocessor-based cardiac device. The device is equipped with multiple sensing and pacing channels which may be physically configured to sense and/or pace multiple sites in the atria or the ventricles. The device shown in FIG. 1 can be configured for cardiac resynchronization pacing of the atria or ventricles. The multiple sensing/pacing channels may be configured, for example, with one atrial and two ventricular sensing/pacing channels for delivering biventricular resynchronization therapy, with the atrial sensing/pacing channel used to deliver the biventricular resynchronization therapy in an atrial tracking mode as well as to pace the atria if required. The controller 10 of the device is a microprocessor which communicates with a memory 12 via a bidirectional data bus. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor.

FIGS. 1B, 1C, 1D and 1E illustrate a heart. As illustrated in FIGS. 1B and 1C, the heart 201 includes a superior vena cava 202, an aortic arch 203, and a pulmonary artery 204. CRM leads pass nerve sites that can be stimulated in accordance with the present subject matter. For example, CRM leads are capable of being intravascularly inserted through a peripheral vein and into the coronary sinus, and are capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. The coronary sinus and pulmonary artery are provided as examples of vasculature proximate to the heart in which a lead can be intravascularly inserted to stimulate nerves within or proximate to the vasculature. Thus, according to various aspects of the present subject matter, parasympathetic nerves are stimulated in or around vasculature located proximate to the heart by at least one electrode intravascularly inserted therein. Alternatively, a wireless stimulating device may be positioned via catheter into the vasculature located proximate to the heart. Control of stimulation and/or energy for stimulation may be supplied by another implantable or external device via ultrasonic, electromagnetic or a combination thereof.

Figure 1E:
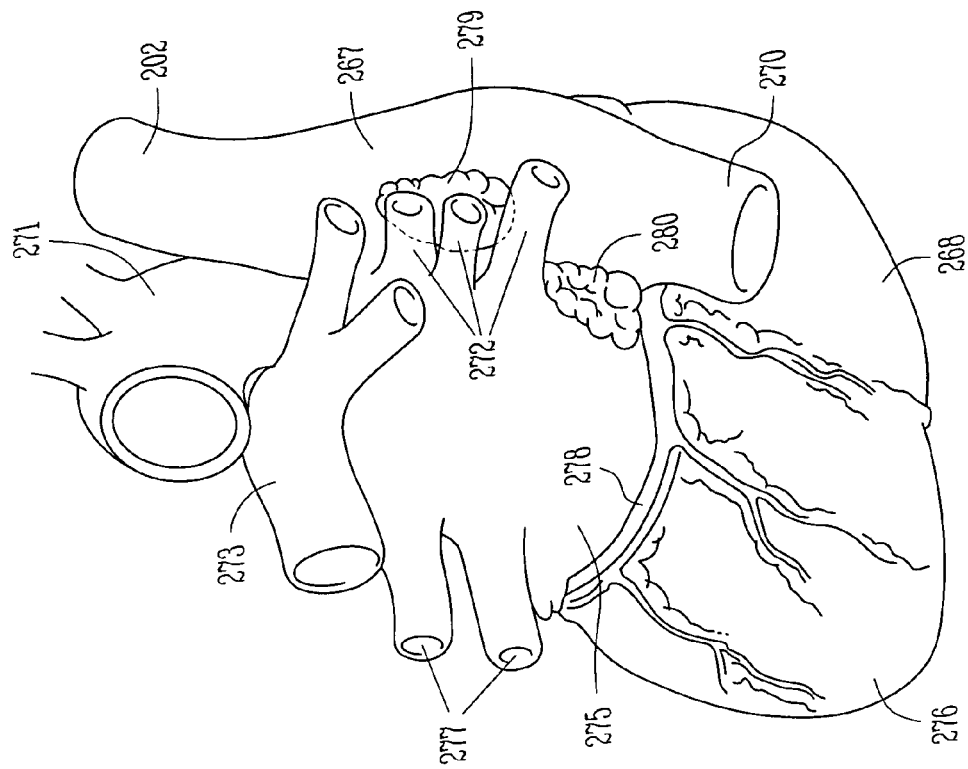
Figure 1D:
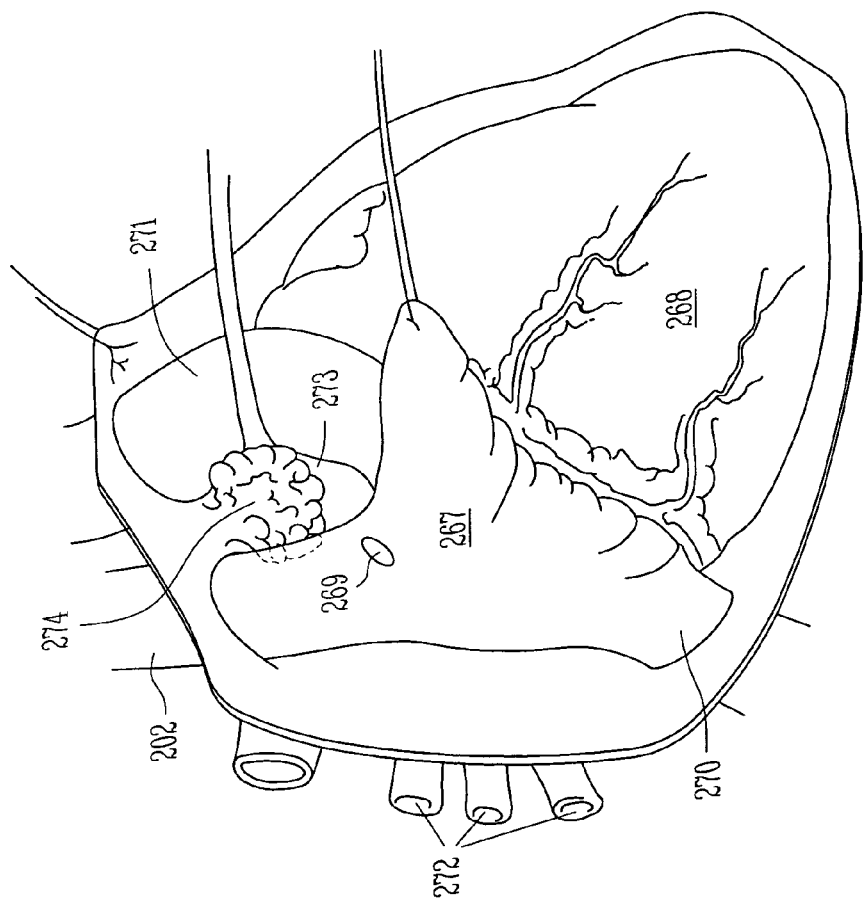

FIGS. 1D and 1E illustrate the right side and left side of the heart, respectively, and further illustrate cardiac fat pads which have nerve endings that function as baroreceptor sites. FIG. 1D illustrates the right atrium 267, right ventricle 268, sinoatrial node 269, superior vena cava 202, inferior vena cava 270, aorta 271, right pulmonary veins 272, and right pulmonary artery 273. FIG. 1D also illustrates a cardiac fat pad 274 between the superior vena cava and aorta. Nerve endings in the cardiac fat pad 274 are stimulated in some embodiments using an electrode screwed into or otherwise placed in the fat pad, and are stimulated in some embodiments using an intravenously-fed lead proximately positioned to the fat pad in a vessel such as the right pulmonary artery or superior vena cava, for example. FIG. 1E illustrates the left atrium 275, left ventricle 276, right atrium 267, right ventricle 268, superior vena cava 202, inferior vena cava 270, aorta 271, right pulmonary veins 272, left pulmonary vein 277, right pulmonary artery 273, and coronary sinus 278. FIG. 1E also illustrates a cardiac fat pad 279 located proximate to the right cardiac veins and a cardiac fat pad 280 located proximate to the inferior vena cava and left atrium. Nerve endings in the fat pad 279 are stimulated in some embodiments using an electrode screwed into the fat pad 279, and are stimulated in some embodiments using an intravenously-fed lead proximately positioned to the fat pad in a vessel such as the right pulmonary artery 273 or right pulmonary vein 272, for example. Nerve endings in the fat pad 280 are stimulated in some embodiments using an electrode screwed into the fat pad, and are stimulated in some embodiments using an intravenously-fed lead proximately positioned to the fat pad in a vessel such as the inferior vena cava 270 or coronary sinus or a lead in the left atrium 275, for example.

Shown in the FIG. 2 are three exemplary sensing and pacing channels designated "A" through "C" comprising bipolar leads with ring electrodes 34A-C and tip electrodes 33A-C, sensing amplifiers 31A-C, pulse generators 32A-C, and channel interfaces 30A-C. Each channel thus includes a pacing channel made up of the pulse generator connected to the electrode and a sensing channel made up of the sense amplifier connected to the electrode. The channel interfaces 30A-C communicate bidirectionally with microprocessor 10, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The electrodes of each bipolar lead are connected via conductors within the lead to a MOS switching network 70 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 80 serving as a ground electrode. A shock pulse generator 60 is also interfaced to the controller for delivering a defibrillation shock via a pair of shock electrodes 61 to the atria or ventricles upon detection of a shockable tachyarrhythmia.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. CRT is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites. An exertion level sensor 330 (e.g., an accelerometer, a minute ventilation sensor, or other sensor that measures a parameter related to metabolic demand) enables the controller to adapt the pacing rate in accordance with changes in the patient's physical activity and, as explained below, can enable the controller to modulate the delivery of neural stimulation and/or cardiac resynchronization pacing. A telemetry interface 82 is also provided which enables the controller to communicate with an external programmer or remote monitor.

Neural stimulation channels are incorporated into the device for delivering parasympathetic stimulation and/or sympathetic inhibition, where one channel includes a bipolar lead with a ring electrode 44 and a tip electrode 43, a pulse generator 42, and a channel interface 40, and the other channel includes a bipolar lead with a ring electrode 54 and a tip electrode 53, a pulse generator 52, and a channel interface 50. Other embodiments may use unipolar leads in which case the neural stimulation pulses are referenced to the can or another electrode. The pulse generator for each channel outputs a train of neural stimulation pulses which may be varied by the controller as to amplitude, frequency, and duty-cycle.

4. Sites for CRT and Neural Stimulation

In various embodiments, a neural stimulation channel uses a lead adapted to be intravascularly disposed to transvascularly stimulate an appropriate nerve, e.g., near a baroreceptor in the case of a sympathetic inhibition channel or near a parasympathetic nerve in the case of a parasympathetic stimulation channel. Some CRT devices include an atrial lead to pace and/or sense the right atrium, a right ventricle lead to pace and/or sense the right ventricle, and a left ventricle lead fed through the coronary sinus to a position to pace and/or sense the left ventricle, such as illustrated in FIGS. 1B and 1C. A lead within the coronary sinus is capable of being used to transvascularly stimulate target parasympathetic nerves anatomically located on the extravascular surface of the coronary sinus at a strength sufficient to elicit depolarization of adjacent nerves, and is also capable of being used to deliver cardiac resynchronization therapy with appropriately timed pacing pulses at a site proximate to the left ventricle, for example.

According to various embodiments, the device is designed to sense a refractory period, and to deliver the neural stimulation from an electrode or electrodes within the coronary sinus during the refractory period to avoid unintentionally capturing cardiac tissue and inducing an arrhythmia such as atrial fibrillation.

Various lead embodiments implement a number of designs, including an expandable stent-like electrode with a mesh surface dimensioned to abut a wall of a predetermined blood vessel, a coiled electrode(s), a fixed screw-type electrode(s), and the like. Various embodiments place the electrode(s) inside the blood vessel, into the wall of the blood vessel, or a combination of at least one electrode inside the blood vessel and at least one electrode into the wall of the blood vessel. The neural stimulation electrode(s) can be integrated into the same lead used for CRT or in another lead in addition to CRT lead(s). In various embodiments, the neural stimulation can be performed by a satellite stimulator located intravascularly and controlled by a planet such as an implantable medical device performing CRT functions.

Transvascular leads can be used to stimulate other nerve sites. For example, an embodiment feeds a transvascular stimulation lead into the right azygos vein to stimulate the vagus nerve; and an embodiment feeds a transvascular stimulation lead into the internal jugular vein to stimulate the vagus nerve. Various embodiments use at least one lead intravascularly fed along a lead path to transvascularly apply neural stimulation and electrically stimulate a cardiac muscle, such as ventricular pacing, as part of CRT.

Other transvascular locations have been mentioned with respect to FIGS. 1D and 1E. Depending on the intravascular location of the neural stimulation electrode(s), the right vagal branch, the left vagal branch or a combination of the right and left vagal branches are capable of being stimulated. The left and right vagal branches innervate different areas of the heart, and thus provide different results when stimulated. According to present knowledge, the right vagus nerve appears to innervate the right side of the heart, including the right atrium and right ventricle, and the left vagus nerve appears to innervate the left side of the heart, including the left atrium and left ventricle. Stimulation of the right vagus has more chronotropic effects because the sinus node is on the right side of the heart. Thus, various embodiments selectively stimulate the right vagus nerve and/or the left vagus nerve to selectively control contractility, excitability, and inflammatory response on the right and/or left side of the heart. Since the venous system is for the most part symmetrical, leads can be fed into an appropriate vessel to transvascularly stimulate the right or left vagus nerve. For example, a lead in the right internal jugular vein can be used to stimulate the right vagus nerve and a lead in the left internal jugular vein can be used to stimulate the left vagus nerve.

The stimulation electrode(s) are not in direct neural contact with the parasympathetic nerve when the transvascular approach to peripheral nerve stimulation is used. Thus, problems associated with neural inflammation and injury commonly associated with direct contact electrodes are reduced.

Various embodiments use at least one lead fed along a lead path and adapted to be epicardially-disposed near an appropriate neural stimulation site for vagal nerves and an appropriate site for electrically stimulating cardiac muscle, such as ventricular pacing, as part of CRT. In various embodiments, a satellite unit to provide neural stimulation is epicardially-disposed near an appropriate neural stimulation site. Such satellite units are capable of being integrated with implantable CRM devices that are performing CRT functions using either epicardial leads or transvascularly-fed leads.

According to various embodiments, the device is designed to sense a refractory period, and to deliver the neural stimulation from an electrode or electrodes within the coronary sinus during the refractory period to avoid unintentionally capturing cardiac tissue and inducing an arrhythmia such as atrial fibrillation. The myelinated vagal nerve fibers of a parasympathetic nervous system is much lower than that of myocardial tissue. Thus, when stimulating these myelinated vagal nerve fibers, parasympathetic stimulation can be applied in the absence of myocardial stimulation.

Figure 3:
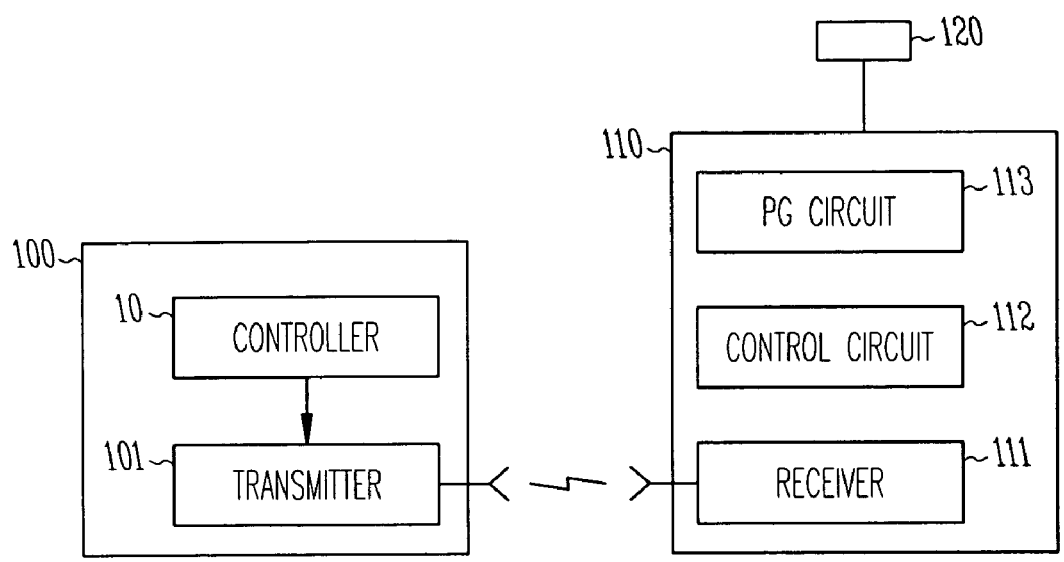
FIG. 3 illustrates an embodiment of an implantable device with RF-controlled satellite units for neural stimulation.

In various embodiments, the leads of the neural stimulation electrodes are replaced by wireless links, and the electrodes for providing parasympathetic stimulation and/or sympathetic inhibition are incorporated into satellite units. The wireless link may be, for example, a radio-frequency (RF) link or an acoustic link. FIG. 1A illustrates a wireless embodiment where the implantable device 100 communicates with such a satellite unit 110 via a wireless transmitter interfaced to the controller. The satellite unit 110 is an integrated assembly adapted for surgical implantation which includes a housing containing a battery and circuitry for outputting neural stimulation pulses to a target nerve (e.g., vagus, carotid sinus, or aortic nerve). FIG. 3 illustrates the functional components of the implantable device 100 and satellite unit 110 relevant to this embodiment. The implantable device includes a wireless transmitter 101 (e.g., either an RF transmitter or an acoustic transducer) interfaced to the controller 10 for transmitting commands, and the satellite unit 110 includes a wireless receiver 111 (e.g., either an RF receiver or a microphone for receiving acoustic signals) interfaced to control circuitry 112 for receiving the commands. The control circuitry 112 translates the received commands and causes pulse generation circuitry 113 to output appropriate stimulation pulses to the external electrode 120.

Increased sympathetic nervous system activity following ischemia often results in increased exposure of the myocardium to epinephrine and norepinephrine. These catecholamines activate intracellular pathways within the myocytes, which lead to myocardial death and fibrosis. Stimulation of the parasympathetic nerves (vagus) inhibits this effect. According to various embodiments, the present subject matter selectively activates the vagal cardiac nerves in addition to CRT in heart failure patients to protect the myocardium from further remodeling and arrhythmogenesis. Other potential benefits of stimulating vagal cardiac nerves in addition to CRT include reducing inflammatory response following myocardial infarction, and reducing the electrical stimulation threshold for defibrillating. For example, when a ventricular tachycardia is sensed, vagal nerve stimulation is applied, and then a defibrillation shock is applied. The vagal nerve stimulation allows the defibrillation shock to be applied at less energy.

5. Assessment of Cardiac Function

In one embodiment of the invention, the delivery of RCT and/or ART is modulated in accordance with an assessment of cardiac function performed by the implantable device. One means by which cardiac function may be assessed is by measuring cardiac output and comparing it with the patient's measured exertion level. Cardiac output may be measured by an impedance technique in which transthoracic impedance is measured and used compute stroke volume. In one embodiment, the exertion level sensor is a minute ventilation sensor which includes an exciter and an impedance measuring circuit. The exciter supplies excitation current of a specified amplitude (e.g., as a pulse waveform with constant amplitude) to excitation electrodes that are disposed in the thorax. Voltage sense electrodes are disposed in a selected region of the thorax so that the potential difference between the electrodes while excitation current is supplied is representative of the transthoracic impedance between the voltage sense electrodes. The conductive housing or can may be used as one of the voltage sense electrodes. The impedance measuring circuitry processes the voltage sense signal from the voltage sense electrodes to derive the impedance signal. Further processing of the impedance signal allows the derivation of signal representing respiratory activity and/or cardiac blood volume, depending upon the location the voltage sense electrodes in the thorax. (See, e.g., U.S. Pat. Nos. 5,190,035 and 6,161,042, assigned to the assignee of the present invention and hereby incorporated by reference.) If the impedance signal is filtered to remove the respiratory component, the result is a signal that is representative of blood volume in the heart at any point in time, thus allowing the computation of stroke volume and, when combined with heart rate, computation of cardiac output. The stroke volume integrated over time (or averaged and multiplied by heart rate) gives the patient's cardiac output. A look-up table or other function may be used to compute what cardiac output is considered adequate for a given exertion level. Measurement of cardiac output or a determination of the adequacy of the cardiac output may be used by the device to modulate the delivery of RCT and/or ART.

Another means for assessing cardiac function is by determining the autonomic balance of the patient. It is well-known that an increase in the activity of the sympathetic nervous system may be indicative of metabolic stress and the need for increased cardiac output. One means by which increased sympathetic activity may be detected is via spectral analysis of heart rate variability. Heart rate variability refers to the variability of the time intervals between successive heart beats during a sinus rhythm and is primarily due to the interaction between the sympathetic and parasympathetic arms of the autonomic nervous system. Spectral analysis of heart rate variability involves decomposing a signal representing successive beat-to-beat intervals into separate components representing the amplitude of the signal at different oscillation frequencies. It has been found that the amount of signal power in a low frequency (LF) band ranging from 0.04 to 0.15 Hz is influenced by the levels of activity of both the sympathetic and parasympathetic nervous systems, while the amount of signal power in a high frequency band (HF) ranging from 0.15 to 0.40 Hz is primarily a function of parasympathetic activity. The ratio of the signal powers, designated as the LF/HF ratio, is thus a good indicator of the state of autonomic balance, with a high LF/HF ratio indicating increased sympathetic activity. An LF/HF ratio which exceeds a specified threshold value may be taken as an indicator that cardiac function is not adequate. A cardiac rhythm management device can be programmed to determine the LF/HF ratio by analyzing data received from its atrial ventricular sensing channels. The intervals between successive atrial or ventricular senses, referred to as beat-to-beat or BB intervals, can be measured and collected for a period of time or a specified number of beats. The resulting series of RR interval values is then stored as a discrete signal and analyzed to determine its energies in the high and low frequency bands as described above. Techniques for estimating the LF/HF ratio based upon interval data are described in commonly assigned U.S. patent application Ser. No. 10/436,876 filed May 12, 2003, and Ser. No. 10/669,170 filed Sep. 23, 2003, the disclosures of which are hereby incorporated by reference.

Other means of assessing cardiac function may also be employed to modulate the delivery of ART and/or RCT. The impedance technique for measuring cardiac output discussed above may also be used to measure ventricular volumes at various stages of the cardiac cycle such as end-diastolic and end-systolic volumes and used to compute parameters reflective of cardiac function such as ejection fraction. The implantable device may also be equipped with other sensing modalities such as a pressure transducer. Such a pressure transducer may be attached to an intravascular lead and be appropriately disposed for measuring diastolic filling pressures and/or systolic pulse pressures.

6. Implementation Examples

In an embodiment of the invention, an implantable device for delivering cardiac therapy to post-MI patients includes one or more pacing channels for delivering pacing pulses to one or more ventricular sites and a sympathetic inhibition channel for stimulating nerves which inhibit sympathetic nerve activity. The controller is programmed to deliver remodeling control therapy (RCT) by delivering ventricular pacing in a cardiac resynchronization mode which pre-excites a region of the ventricular myocardium so as to mechanically unload that region during systole. The cardiac resynchronization therapy may be delivered as biventricular pacing where one of the ventricles is pre-excited relative to the other as determined by a programmed biventricular offset interval. Alternatively, in patients suffering from delayed activation of the left ventricle, a left ventricle-only resynchronization pacing mode may be employed. In another embodiment, the pacing therapy may be delivered as multi-site ventricular pacing where at least one of the ventricles is paced at a plurality of sites so as to pre-excite one or more of the sites relative to the other sites. In any case, the ventricular pacing may be delivered in a non-atrial tracking mode where a ventricular escape interval is defined between ventricular paces, or in an atrial tracking mode where the ventricular paces are delivered after a defined atrio-ventricular escape interval following an atrial sense. In a patient who is chronotropically incompetent, an atrial pacing channel may also be provided for pacing the atria, with the ventricular pace(s) delivered upon expiration of the atrio-ventricular escape interval following the atrial pace.

The controller is further programmed to delivery anti-remodeling therapy (ART) in conjunction with the RCT by inhibiting sympathetic nerve activity via the sympathetic inhibition channel. The sympathetic inhibition channel may include a pulse generator for outputting neural stimulation pulses and a lead incorporating an electrode adapted for disposition near an arterial baroreceptor or afferent nerve of a baroreflex arc. Stimulation of the baroreflex arc then results in inhibition of sympathetic activity. The electrode of the sympathetic inhibition channel may be intravascularly positioned in a blood vessel or elsewhere proximate to a baroreceptor or afferent nerve such as in a pulmonary artery or a cardiac fat pad. In another embodiment, the device may further include a parasympathetic stimulation channel, where the anti-remodeling therapy delivered by the controller further includes stimulation of parasympathetic nerve activity, and the parasympathetic stimulation channel includes a pulse generator for outputting neural stimulation pulses and an electrode for stimulating a parasympathetic nerve. The electrode may be a nerve cuff electrode adapted for disposition around a parasympathetic nerve or an intravascular electrode for transvascularly stimulating a parasympathetic nerve adjacent to a blood vessel. As described above, for either the sympathetic inhibition channel or the parasympathetic stimulation channel, the electrode and pulse generator may also be incorporated into a satellite unit which includes an RF receiver. The implantable device then further comprises an RF transmitter interfaced to the controller for controlling the operation of the satellite unit via an RF link.

Figure 4A:
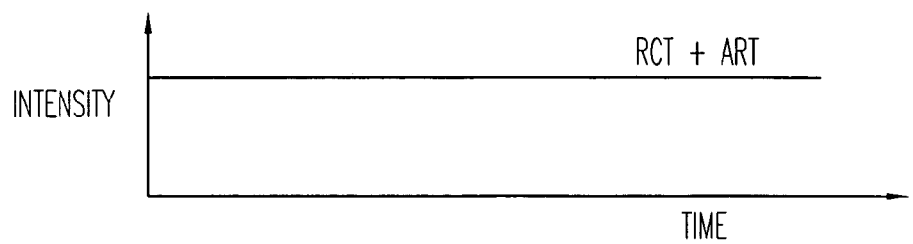
FIGS. 4A-D illustrate examples of how the intensities of ART and RCT may be individually time-varied.
Figure 4B:
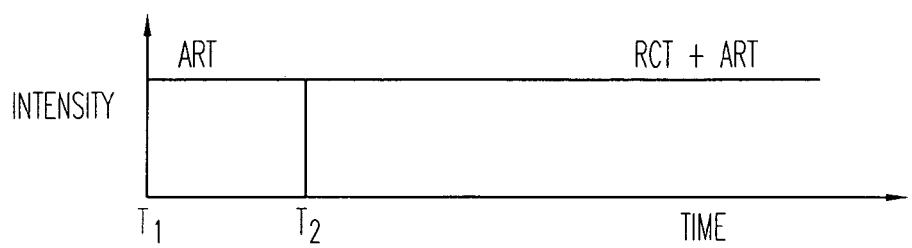
Figure 4C:
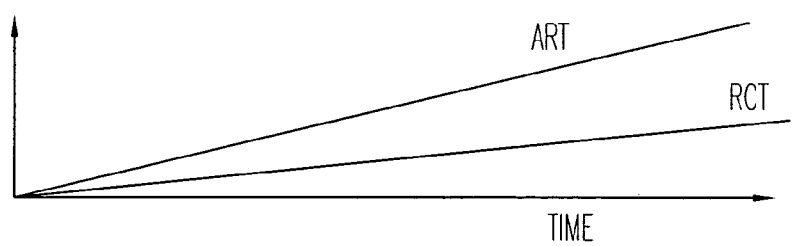
Figure 4D:
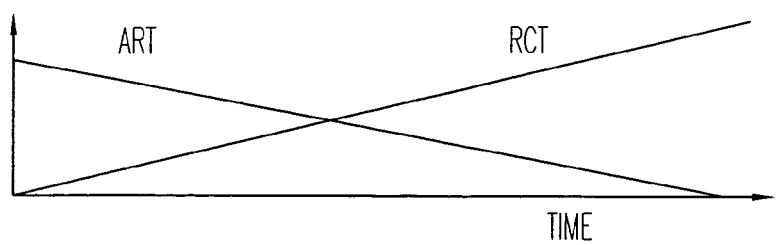

The device may be programmed to deliver RCT and ART in open-loop fashion where the RCT and ART are delivered simultaneously or separately at programmed intervals. The RCT and ART may be delivered at a constant or time-varying intensity, where the intensity of the ART may be adjusted by varying the amplitude, frequency, or duty-cycle of the neural stimulation pulses, and the intensity of the RCT may be adjusted by varying one or more parameters which affect the amount of pre-excitation delivered to the ventricles such as the biventricular offset interval and the atrio-ventricular escape interval. FIGS. 4A through 4D illustrate examples of how the level of RCT and ART may be varied with respect to time. In FIG. 4A, both RCT and ART are delivered simultaneously with each type of therapy maintained at a constant intensity. In FIG. 4B, both RCT and ART are delivered at a constant intensity, but ART starts at a time $T_1$ while RCT starts at a time $T_2$. In FIGS. 4C and 4D, the intensity of each type of therapy is modulated with respect to time. FIG. 4C shows the intensity of both the RCT and ART increasing with respect to time, while FIG. 4D shows the intensity of the RCT increasing while the intensity of the ART decreases. The relative intensities of sympathetic inhibition and parasympathetic stimulation may also be separately modulated.

In another embodiment, the device is programmed to deliver RCT and ART in closed-loop fashion, where the intensities of RCT and ART are modulated in accordance with an assessment of cardiac function performed by the controller. The device may also separately modulate the intensities of parasympathetic stimulation and sympathetic inhibition which are delivered as part of the ART in accordance with the assessment of cardiac function. Cardiac function may be assessed by the device using several different modalities, either alone or in combination. In one embodiment, the device incorporates a sensor for measuring cardiac output, and the controller is programmed to modulate the delivery of RCT and ART in accordance with the measured cardiac output. As described above, such a cardiac output sensor may be a transthoracic impedance measuring circuit. Another means for assessing cardiac function is an arterial blood pressure sensor, where the controller is programmed to modulate the delivery of RCT and ART in accordance with the measured blood pressure. The blood pressure sensor may take the form of a pressure transducer and lead adapted for disposition within an artery. Alternatively, a measure of the patient's respiratory activity taken by a minute ventilation sensor may be used as a surrogate for blood pressure. Cardiac function may also be assessed by measuring the patient's exertion level (e.g., using either a minute ventilation sensor or an accelerometer) together with a measure of cardiac output and/or blood pressure, where the controller is then programmed to modulate the delivery of RCT and ART in accordance with the combined measurements.

In another embodiment, the cardiac function assessment includes an assessment of the patient's autonomic balance. Autonomic balance may be assessed directly with a sensing channel for measuring electrical activity in sympathetic and parasympathetic nerves with appropriately positioned sensing electrodes, or if the patient is chronotropically competent, by measuring the intrinsic heart rate. As described above, measuring heart rate variability provides one means for assessing autonomic balance. Thus, the device may include circuitry for measuring and collecting time intervals between successive intrinsic beats, referred to as a BB interval, where the BB interval may be an interval between successive atrial or ventricular senses. The device stores the collected intervals as a discrete BB interval signal, filters the BB interval signal into defined high and low frequency bands, and determines the signal power of the BB interval signal in each of the low and high frequency bands, referred to LF and HF, respectively. The device then computes an LF/HF ratio and assesses autonomic balance by comparing the LF/HF ratio to a specified threshold value.

In certain embodiments, data gathered by the device in performing the assessment of cardiac function performed is transmitted to a remote monitor via an RF telemetry link. The remote monitor may record the data for later analysis by a clinician and/or transmit it to another location over a network such as the internet. In response to network communications, the remote monitor may also program the implantable device via the RF telemetry link in order to modify the delivery of RCT and ART.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. An implantable device for delivering cardiac therapy to a patient, comprising:
    a plurality of leads, including at least one lead to be positioned within a lead path to deliver ventricular pacing pulses from the lead path and to deliver neural stimulation from the lead path at a site proximate to the heart to inhibit sympathetic nerve activity; and
        a controller to control delivery of the ventricular pacing pulses in accordance with a programmed pacing mode and to control delivery of the neural stimulation, the controller being programmed to deliver remodeling control therapy (RCT) by delivering ventricular pacing to pre-excite a ventricular myocardium region to mechanically unload that region during systole, and further being programmed to deliver anti-remodeling therapy (ART) by delivering neural stimulation to inhibit sympathetic nerve activity in conjunction with RCT.

2. The device of claim 1, wherein the at least one lead to be positioned within the lead path includes at least one lead to be positioned to epicardially deliver ventricular pacing pulses and epicardially deliver neural stimulation at the site proximate to the heart to inhibit sympathetic nerve activity.

3. The device of claim 2, wherein the controller is programmed to deliver neural stimulation during a cardiac refractory period.

4. The device of claim 1, wherein the at least one lead to be positioned within the lead path includes at least one intravascular lead to deliver ventricular pacing pulses and deliver neural stimulation at the site proximate to the heart to inhibit sympathetic nerve activity.

5. The device of claim 4, wherein the at least one intravascular lead includes at least one intravascular lead adapted to be fed through a coronary sinus to deliver ventricular pacing pulses, the at least one lead including at least one electrode to transvascularly deliver the neural stimulation from the coronary sinus.

6. The device of claim 5, wherein the controller is programmed to deliver neural stimulation from the coronary sinus using the at least one electrode during a cardiac refractory period.

7. The device of claim 1, wherein the at least one intravascular lead includes an expandable electrode with a mesh surface dimensioned to abut a wall of a predetermined blood vessel.

8. The device of claim 1, wherein the controller is programmed to deliver RCT and ART simultaneously.

9. The device of claim 1, wherein the controller is programmed to coordinate and deliver RCT and ART at separate times.

10. The device of claim 1, further comprising means for assessing cardiac function and wherein the controller is programmed to adjust delivery at least one of RCT and ART based on an assessment of cardiac function.

11. The device of claim 10, wherein the cardiac function assessing means comprises a sensor for measuring cardiac output and wherein the controller is programmed to adjust delivery at least one of RCT and ART in accordance with the measured cardiac output.

12. The device of claim 10, wherein the cardiac function assessing means comprises an arterial blood pressure sensor and wherein the controller is programmed to adjust delivery at least one of RCT and ART in accordance with the measured blood pressure.

13. The device of claim 10, wherein the cardiac function assessing means comprises an exertion level sensor for measuring the patient's exertion level, and wherein the controller is programmed to modulate the delivery of RCT and ART in accordance with the measured exertion level.

14. The device of claim 10, wherein the cardiac function assessment means includes a sensing channel for measuring autonomic balance and wherein the cardiac function assessment includes an assessment of the patient's autonomic balance, further comprising:
    circuitry for measuring and collecting time intervals between successive intrinsic beats, referred to as a BB interval, and storing the collected intervals as a discrete BB interval signal, filtering the BB interval signal into defined high and low frequency bands, and determining the signal power of the BB interval signal in each of the low and high frequency bands, referred to LF and HF, respectively; and
    circuitry for computing an LF/HF ratio and assessing autonomic balance by comparing the LF/HF ratio to a specified threshold value.

15. The device of claim 10, wherein RCT is adjusted in response to the assessment of cardiac function by varying the extent of pre-excitation provided to a ventricular pacing site.

16. The device of claim 10, wherein ART is adjusted in response to the assessment of cardiac function by varying the amplitude of neural stimulation pulses.

17. The device of claim 10, wherein ART is adjusted in response to the assessment of cardiac function by varying the frequency of neural stimulation pulses.

18. The device of claim 10, wherein ART is adjusted in response to the assessment of cardiac function by varying the duty cycle of neural stimulation pulses.

19. The device of claim 1, further comprising:
    a sensing channel for detecting intrinsic cardiac activity;
    a shock channel for delivering a cardioversion/defibrillation shock pulse; and,
    wherein the controller is programmed to deliver a shock pulse upon detection of a tachyarrhythmia above a specified rate threshold.

20. The device of claim 1, wherein the controller is programmed to deliver RCT as biventricular pacing so as to pre-excite one of the ventricles relative to the other.

21. The device of claim 1, wherein the controller is programmed to deliver RCT as multi-site ventricular pacing where at least one of the ventricles is paced at a plurality of sites so as to pre-excite one or more of the sites relative to the other sites.

22. The device of claim 1, wherein the controller is programmed to deliver RCT as left ventricle-only pacing which pre-excites the left ventricle relative to the right ventricle during systole.

23. An implantable device for delivering cardiac therapy to a patient, comprising:
    a number of leads, each with at least one electrode, to provide one or more pacing channels to deliver ventricular pacing pulses to one or more ventricular sites, and a sympathetic inhibition channel to stimulate nerves to inhibit sympathetic nerve activity, the number of leads including an intravascularly-fed lead to both transvascularly stimulate the nerves to inhibit sympathetic nerve activity and deliver ventricular pacing pulses;

a controller for controlling the delivery of pacing pulses to one or more ventricular sites during a cardiac cycle in accordance with a programmed pacing mode;

wherein the controller is programmed to deliver remodeling control therapy (RCT) by delivering ventricular pacing in a manner which pre-excites a region of the ventricular myocardium to mechanically unload that region during systole, and to deliver anti-remodeling therapy (ART) in conjunction with RCT by inhibiting sympathetic nerve activity via the sympathetic inhibition.

24. The device of claim 23, wherein the at least one intravascularly-fed lead includes a lead to be fed through a coronary sinus with at least one electrode to transvascularly stimulate nerves located on an extravascular surface of the coronary sinus.

25. The device of claim 23, wherein the programmer is further programmed to deliver baroreflex stimulation to inhibit sympathetic nerve activity during a cardiac refractory period to avoid capturing cardiac tissue and inducing an arrhythmia.

26. The device of claim 23, further comprising a parasympathetic stimulation channel for stimulating parasympathetic nerve activity and wherein the anti-remodeling therapy delivered by the controller further includes stimulation of parasympathetic nerve activity.

27. The device of claim 26, wherein the parasympathetic stimulation channel includes a nerve cuff electrode adapted for disposition around a parasympathetic nerve.

28. The device of claim 23, wherein the electrode is incorporated into a satellite unit adapted to be intravascularly positioned.

29. The device of claim 23, wherein the at least one intravascularly-fed lead includes an expandable electrode with a mesh surface dimensioned to abut a wall of a predetermined blood vessel.

30. An implantable device for delivering cardiac therapy to a patient, comprising:
a number of leads, each with at least one electrode, to provide one or more pacing channels to deliver ventricular pacing pulses to one or more ventricular sites, and a sympathetic inhibition channel to stimulate nerves to inhibit sympathetic nerve activity, the number of leads including a lead to both epicardially stimulate the nerves to inhibit sympathetic nerve activity and epicardially deliver ventricular pacing pulses;

a controller for controlling the delivery of pacing pulses to one or more ventricular sites during a cardiac cycle in accordance with a programmed pacing mode;

wherein the controller is programmed to deliver remodeling control therapy (RCT) by delivering ventricular pacing in a manner which pre-excites a region of the ventricular myocardium to mechanically unload that region during systole, and to deliver anti-remodeling therapy (ART) in conjunction with RCT by inhibiting sympathetic nerve activity via the sympathetic inhibition channel.

31. The device of claim 30, wherein the programmer is further programmed to deliver baroreflex stimulation to inhibit sympathetic nerve activity during a cardiac refractory period to avoid capturing cardiac tissue and inducing an arrhythmia.

32. The device of claim 30, further comprising a parasympathetic stimulation channel for stimulating parasympathetic nerve activity and wherein the anti-remodeling therapy delivered by the controller further includes stimulation of parasympathetic nerve activity.

33. The device of claim 32, wherein the parasympathetic stimulation channel includes a nerve cuff electrode adapted for disposition around a parasympathetic nerve.

34. The device of claim 30, wherein the electrode is incorporated into a satellite unit adapted to be intravascularly positioned.

35. A method for delivering cardiac therapy to a patient, comprising:
routing a plurality of leads adapted to provide cardiac pacing as part of a cardiac resynchronization therapy (CRT) and to provide neural stimulation, including routing at least one of the leads through a lead path;

delivering CRT, including delivering cardiac pacing signals using the lead path to pace cardiac tissue; and delivering neural stimulation signals using the lead path to inhibit sympathetic nerve activity, wherein delivering neural stimulation signals includes delivering neural stimulation signals during a cardiac refractory period to avoid capturing cardiac tissue.

36. The method of claim 35, wherein delivering cardiac pacing signals includes delivering cardiac pacing signals over a first lead using the lead path, and delivering neural stimulation signals includes delivering neural stimulation signals over a second lead using the lead path.

37. The method of claim 35, wherein delivering cardiac pacing signals includes delivering cardiac pacing signals over a first lead using the lead path, and delivering neural stimulation signals includes delivering neural stimulation signals over the first lead using the lead path.

38. The method of claim 35, wherein the lead path includes a lead path to deliver cardiac pacing signals and delivering neural stimulation signals epicardially.

39. The method of claim 35, wherein the lead path includes an intravascular lead path.

40. The method of claim 35, further comprising expanding an expandable stent-like electrode within a blood vessel.

41. The method of claim 35, further comprising coordinating delivering CRT and delivering neural stimulation signals to provide a ventricular remodeling treatment.

42. The method of claim 35, further comprising sensing a cardiac refractory period, wherein delivering neural stimulation signals includes delivering neural stimulation signals during the cardiac refractory period.

* * * * *

UNITED STATES PATENT AND TRADEMARK OFFICE
CERTIFICATE OF CORRECTION

PATENT NO.       : 7,587,238 B2
APPLICATION NO.  : 11/078460
DATED            : September 8, 2009
INVENTOR(S)      : Moffitt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 935 days.

Signed and Sealed this

Twenty-first Day of September, 2010

David J. Kappos
*Director of the United States Patent and Trademark Office*

UNITED STATES PATENT AND TRADEMARK OFFICE
CERTIFICATE OF CORRECTION

PATENT NO. : 7,587,238 B2  
APPLICATION NO. : 11/078460  
DATED : September 8, 2009  
INVENTOR(S) : Moffitt et al.

It is certified that error appears in the above-identified patent and that said Letters Patent is hereby corrected as shown below:

In column 2, line 23, delete "andior" and insert -- and/or --, therefor.

In column 2, line 41, delete "barorecptors" and insert -- baroreceptors --, therefor.

In column 13, line 47, in Claim 7, delete "claim 1," and insert -- claim 4, --, therefor.

In column 15, line 10, in Claim 23, delete "inhibition." and insert -- inhibition channel. --, therefor.

Signed and Sealed this  
Third Day of May, 2011

David J. Kappos  
*Director of the United States Patent and Trademark Office*